Figure 1:
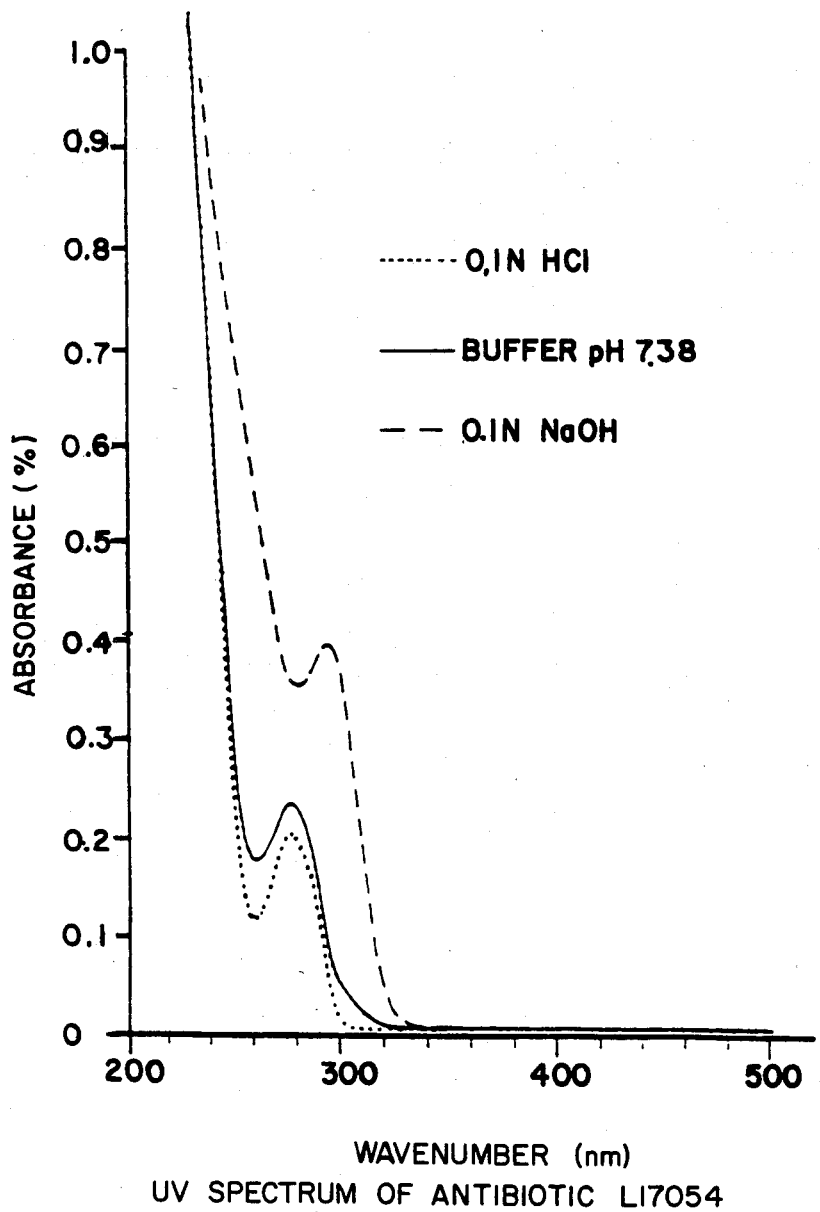

United States Patent [19]

Strazzolini et al.

[11] Patent Number: 4,594,187

[45] Date of Patent: Jun. 10, 1986

[54] PROCESS FOR PREPARING ANTIBIOTIC L 17054

[75] Inventors: Paolo Strazzolini, Fiume Veneto; Adriano Malabarba; Bruno Cavalleri, both of Milan, all of Italy

[73] Assignee: Gruppo Lepetit S.p.A., Milan, Italy

[21] Appl. No.: 680,460

[22] Filed: Dec. 11, 1984

[30] Foreign Application Priority Data

Dec. 16, 1983 [GB] United Kingdom ............... 8333624

[51] Int. Cl.$^4$ .................... C07C 103/52; C07H 15/26
[52] U.S. Cl. .................................. 530/332; 536/7.1; 536/7.5; 536/16.8
[58] Field of Search ............... 536/7.1, 7.2, 7.5, 16.8; 260/112.5 R

[56] References Cited

U.S. PATENT DOCUMENTS

| | | | |
|---|---|---|---|
| 4,196,280 | 4/1980 | Umezawa et al. | 536/7.1 |
| 4,401,660 | 8/1983 | Kirst | 536/7.1 |
| 4,439,426 | 3/1984 | Toscano et al. | 536/7.2 |
| 4,486,584 | 12/1984 | Baltz et al. | 536/7.1 |

OTHER PUBLICATIONS

Majer et al., "Jour. of the American Chemical Soc.", vol. 99, No. 5, 3/1977.

Primary Examiner—Johnnie R. Brown
Attorney, Agent, or Firm—Stephen L. Nesbitt; William J. Stein

[57] ABSTRACT

The present invention is directed to a chemical process for preparing the antibiotic substance denominated antibiotic L 17054 and its pharmaceutically acceptable salts by selectively hydrolyzing teicoplanin or a factor or component thereof with a concentrated strong organic acid.

9 Claims, 3 Drawing Figures

UV SPECTRUM OF ANTIBIOTIC L17054

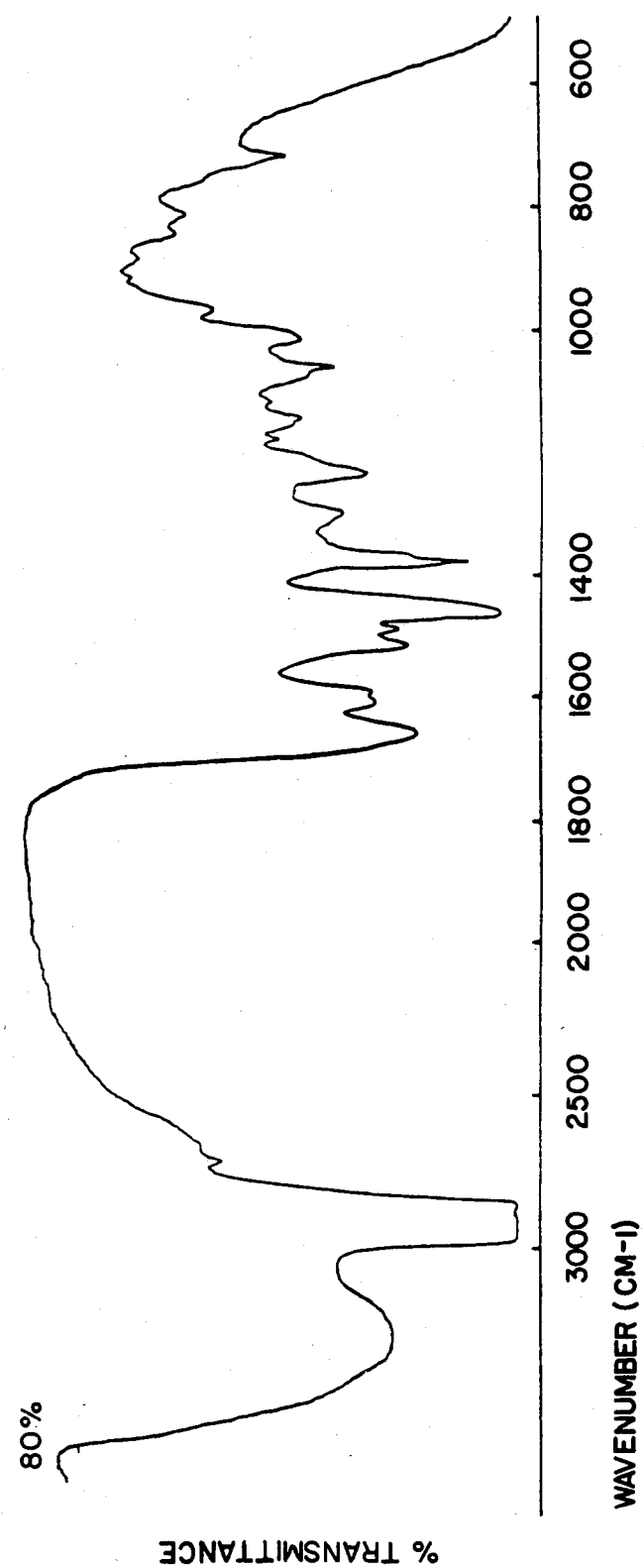
FIG. 2 IR SPECTRUM OF ANTIBIOTIC L17054

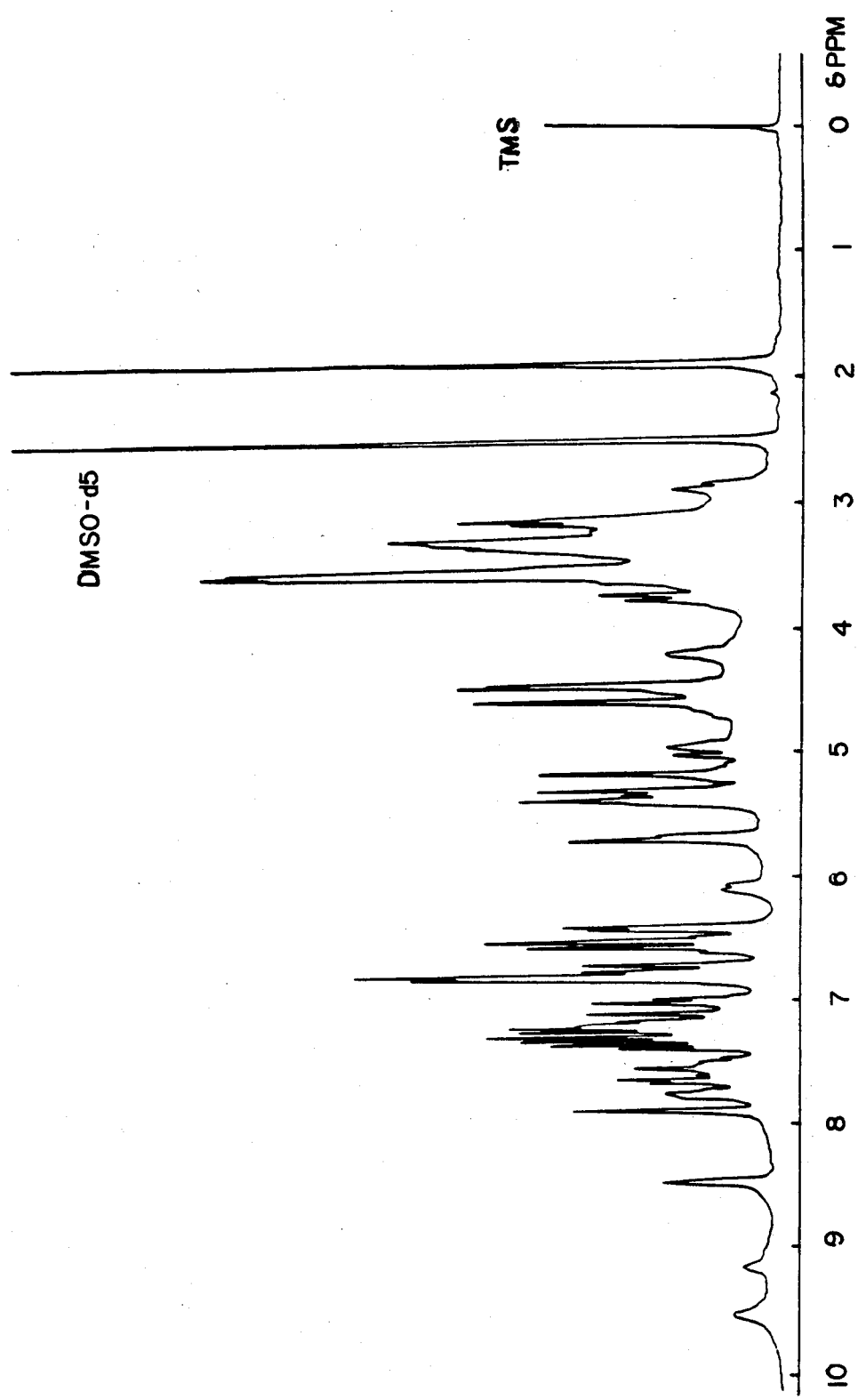

PROCESS FOR PREPARING ANTIBIOTIC L 17054

The present invention is directed to a chemical process for preparing the antibiotic substance arbitrarily designated antibiotic L 17054. This substance may be represented by the following formula I wherein A represents hydrogen, B is N-acetyl-β-D-glucosaminyl and Z is α-D-mannosyl:

As already shown, antibiotic L 17054 is represented by the above formula I wherein A represents hydrogen, B is N-acetyl-β-D-glucosaminyl and Z is α-D-mannosyl and these sugar moieties are linked to the peptidic nucleous through O-glycosidic bonds.

According to the process of the invention, crude or purified teicoplanin, or an isolated factor or component thereof or a mixture of any of these factors or components in any proportion, is reacted with a strong aque-

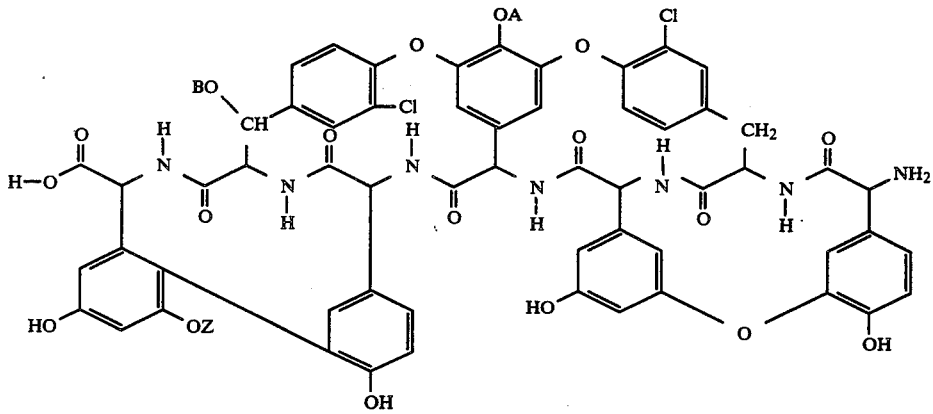

This antibiotic substance possesses antimicrobial activity mainly against gram-positive bacteria (Staphylococci and Streptococci) and is disclosed in the copending European patent application No. 84102666.

The chemical transformation process of the invention includes submitting the antibiotic substance called teicoplanin or factors or components thereof to controlled acid hydrolysis.

Teicoplanin is the international non-proprietary name (INN) of the antibiotic substance formely named teichomycin which is obtained by cultivating the strain *Actinoplanes teicomyceticus* nov. sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures. Teichomycin $A_2$, which is the major factor of the isolated antibiotic complex, is then separated from the other factors $A_1$ and $A_3$ by means of column chromatography on Sephadex ®.

British Patent Application Publication No. 2121401 discloses that antibiotic Teichomycin $A_2$ actually is a mixture of five closely related co-produced main components.

According to recent structural studies it is possible to represent teicoplanin $A_2$ (formerly Teichomycin $A_2$) main components 1, 2, 3, 4 and 5 by the above formula I wherein A is N[($C_{10}$–$C_{11}$)aliphatic acyl]-β-D-glucosaminyl group, B is a N-acetyl-β-glucosaminyl group and Z is an α-D-mannosyl group. All these sugar moieties, when present, are linked to the teicoplanin nucleus through O-glycosidic bonds.

Representative and preferred examples of ($C_{10}$–$C_{11}$)aliphatic acyl groups are n-decanoyl, 8-methylnonanoyl, Z-4-decenoyl, 8-methyldecanoyl, and 9-methyldecanoyl groups.

ous organic acid at about room temperature to obtain antibiotic L 17054.

To facilitate the discussion, in the present specification any one of the above starting materials, i.e. teicoplanin complex as obtained according to U.S. Pat. No. 4,239,751, any crude preparation or any further purification and factors thereof, a compound of the above formula I wherein A represents a [($C_{10}$–$C_{11}$)aliphatic acyl]-β-D-glucosaminyl, B represents N-acetyl-β-D-glucosaminyl, and Z represents α-D-mannosyl, or any mixture thereof in any proportion will be generally referred to as a "starting material."

As it can be seen from formula I, the transformation of a starting material into antibiotic L 17054 essentially involves the cleavage of an O-glycosidic bond, i.e. removing the N-acyl-D-glucosamine group which is represented by A in the above formula I.

It is apparent to the man skilled in the art that the selective cleavage of a O-glycosidic bond in the presence of other two O-glycosidic bonds and on a substrate with many chiral centers presents considerable difficulties. In many instances it is not possible to find the reaction conditions, if any, that can lead to the production of the desired product selectively enough to avoid by-products due to a non-complete hydrolysis of the interested glycosidic bond or due to a partial hydrolysis of other bonds in the molecule or even due to changes in the stereochemical configuration of chiral centers.

An object of the invention is therefore to offer a selective and convenient process for preparing antibiotic L 17054—substantially free from contaminant by-products co-produced during the reaction process—submitting one or more of the above individuated starting materials to a selective hydrolysis in the presence of a concentrated strong aqueous organic acid at about room temperature.

More particularly, the strong aqueous acid of choice in the process of the invention is concentrated trifluoroacetic acid, even if other concentrated similar organic acids may be used.

Very good results are obtained by using aqueous trifluoroacetic acid at a concentration of about 90%, while good results are obtained also by using aqueous trifluoroacetic acid at a concentration between 75% and 95%. The reaction temperature is preferably room temperature. It may generally be in the range from 10° C. to 50° C. and preferably between 15° C. and 35° C., while the most preferred temperature range is 20°-30° C.

As it is known in the art, the reaction time varies considerably depending on the specific reaction conditions used, but generally it is between 30 min. and 4 h. In any case, since the reaction course may be easily monitored by TLC or HPLC techniques, using UV or bioassay on susceptible microorganisms as the detection system, the man skilled in the art is capable of determining the reaction time and ascertain when the reaction is completed. The yields of the process are generally very high and usually are higher than 80% and usually between 90% and 95% or more, calculated on the basis of the molar amount of starting materials.

Depending on the purity of the starting material, antibiotic L 17054 as obtained according to the process of the invention may be pure enough or may need further purification. Usual purification techniques such as precipitation by addition of non-solvents, e.g. alkyl ethers, precipitation by adjusting the pH of an aqueous solution to the isoelectric point, extraction with solvents, and chromatographic techniques may be used. A preferred purification procedure involves the use of a reverse phase column chromatography. A preferred adsorbent in this case is the silanized silica gel having a distribution particle range of 0.06-0.2 mm. The eluent can be one of the hydrophilic mixtures that can be used in this purification technique. Representative examples of these hydrophilic eluents are the mixtures of diluted aqueous solution of ammonium salts of organic acids, acetonitrile or water soluble lower alkanols. Representative examples of diluted aqueous solutions of ammonium salts of organic acids are 0.1–6% ammonium formate aqueous solutions, while examples of suitable alkanols are methanol, ethanol, propanol and the like. Preferred eluents are mixtures of aqueous ammonium formate and acetonitrile at a pH between 6 and 8 or mixtures of aqueous ammonium formate and methanol. Particularly preferred for the purification of crude antibiotic L 17054 is a procedure which includes a first reverse phase chromatography on silanized silica gel (0.06-0.2 mm) developing with a linear step gradient from 5 to 21% acetonitrile in 0.2% aqueous ammonia formate and a second column chromatography on silanized silica gel (0.06-0.2 mm) which uses a mixture acetonitrile/water, 1:1 as the eluent.

The term "essentially pure", as referred to an antibiotic substance of the present disclosure, refers to substances having an HPLC titre greater than 95% (percent peak areas, at a pre-determined 254 nm UV wavelength), a maximum water and solvents content from 10% to 15% (by weight) and an inorganic residue lower than 0.5% (by weight).

PHYSICO-CHEMICAL CHARACTERISTICS OF ANTIBIOTIC L 17054.

(a) the specific rotation $[\alpha]_D^{20}$ is $-34°$ C. (c=1%, DMF)

(b) it is freely soluble in water at pH>8.0, in dimethylformamide, dimethylsulfoxide, propyleneglycol and methylcellosolve; slightly soluble in methanol; almost insoluble in ethyl ether and acetone.

(c) an ultraviolet absorption spectrum, shown in FIG. 1, which has the following absorption maxima:
in 0.1N hydrochloric acid:
$\lambda_{max}$ 278 nm ($E_{1\ cm}^{1\%}$ = 60.6)
in 0.1N sodium hydroxide:
$\lambda_{max}$ 297 nm ($E_{1\ cm}^{1\%}$ = 118.8)
in phosphate buffer pH 7.4:
$\lambda_{max}$ 277 nm ($E_{1\ cm}^{1\%}$ = 70.3)

(d) an infrared absorption spectrum, shown in FIG. 2, in nujol with the following absorption maximum ($cm^{-1}$): 3700-2000, 2970-2850 (nujol), 1655, 1610, 1595, 1515, 1490, 1460 (nujol), 1375 (nujol), 1300, 1230, 1145, 1060, 1020, 970, 890, 850, 820, 720 (nujol)

(e) an elemental analysis, after the sample has been previously dried at about 140° C. under inert atmosphere (weight loss =7.8%), which indicated the following approximate percentage composition (average): carbon 55.46%; hydrogen, 4.50%; nitrogen 7.20%; chlorine 4.67%; ashes 0.2%

(f) it has the following $R_f$ values in the TLC systems indicated below:

| | Elution system (v/v) | $R_f$ value |
|---|---|---|
| (I) | Acetonitrile/water 75:25 (silica gel Merck 60 F$_{254}$) | 0.32 |
| (II) | Acetonitrile/5% aqueous sodium sulfate 30:70 (silica gel Merck silanized 60 F$_{254}$) Visualization: UV-light at 254 nm; 3% ethanolic ninhydrine; 1% methanolic fluorescamine; | 0.61 |

(g) a retention time ($t_R$) of 8.3 minutes when analyzed by HPLC using a 150×4.0 mm Zorbax ® ODS (5–6 μm) column (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$/acetonitrile 9:1, buffered at pH 6.0 with 0.1N NaOH; solution B: 25 mM NaH$_2$PO$_4$/acetonitrile 3:7, buffered at pH 6.0 with 0.1N NaOH), with a flow rate of 2 ml/min.; (internal standard: 3,5-dihydroxytoluene $t_R$ 5.60 minutes)

(h) the $^1$H NMR spectrum, shown in FIG. 3, is registered at 270 MHz in DMSO-d$_6$ at 60° C. and with a sample concentration of 20 mg/ml (internal standard TMS, $\delta$=0.00 ppm).

Some of the $^1$H NMR data obtained after D$_2$O exchange and selective decoupling experiments are as follows ($\delta$ppm, multiplicity): 1.88, s; 2.85, d; ~3.5, dd; 3–4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s 6.74, d; 6.77, s; 6.80, s; 6.80, d; 6.98, d; 7.08, s; 7.15, d; 7.21, d; 7.28, d; 7.35, d; 7.50, d; 7.64, d; 7.73, d; 7.86, s; 8.42, d.

(i) a potentiometric titration profile which shows three titration slopes with pH½ values equal to 5.0 (one equivalent), 7.0 (one equivalent), and 11 (five equivalents) in methylcellosolve/water 4:1 upon titrating a solution of the test compound containing an excess of 0.01N HCl in methylcellosolve/water 4:1 with 0.01N NaOH in the same solvent mixture (l) an acidic function capable of forming salts (m) a basic function capable of forming salts (n) two sugar residues which are α-D-mannose and N-acetyl-β-D-glucosamine.

On the basis of the physico-chemical data and by comparison with the structures known for other glycopeptidic antibiotic substances, such as vancomycin and ristocetin, the following structure can be attributed to antibiotic L 17054:

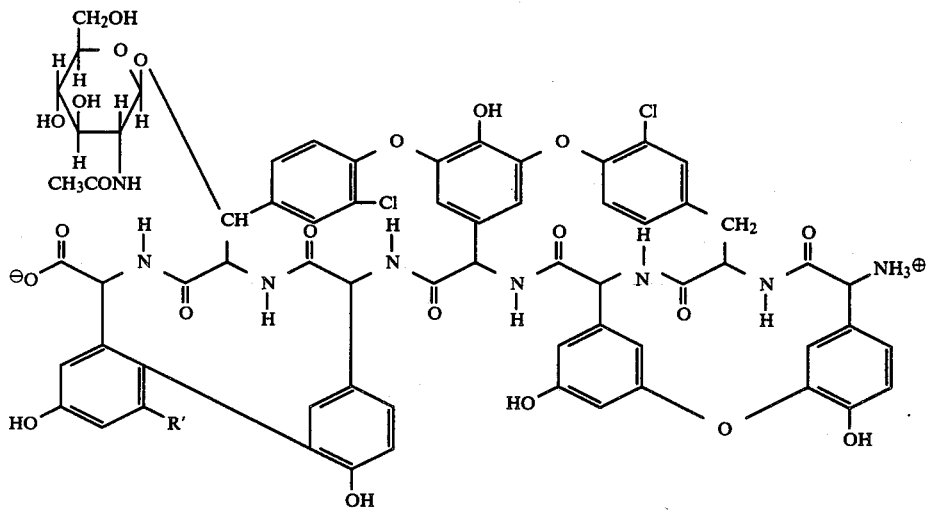

wherein R' represents the group of formula

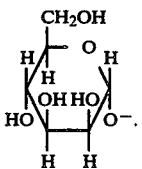

The following examples further illustrate the invention and as such should not be construed as limiting its overall scope.

EXAMPLE 1

Preparation of antibiotic L 17054 from Teicoplanin

Essentially pure teicoplanin (11 g) is added to 90% aqueous trifluoroacetic acid (100 ml) and the mixture is stirred for about 2 hours at room temperature. Then it is poured into 400 ml of ice-cooled ethyl ether. The obtained precipitate is recovered by filtration, washed with ethyl ether and dried in the air, obtaining a powder which is the trifluoroacetic acid addition salt of antibiotic L 17054 (10.5 g).

A portion of the above obtained product (3 g) is suspended in 150 ml of a mixture of 0.2% aqueous ammonium formate and acetonitrile, 95:5 and the pH is brought to about 7.5 with 1N sodium hydroxide. The resulting solution is applied to a silanized silica gel chromatographic column (0.06–0.2 mm; Merck) containing 150 g of the adsorbent prepared in the same solvent mixture. The column is developed with a linear gradient from 5 to 21% acetonitrile in 0.2% aqueous ammonium formate, collecting fractions of 20 ml each, which are assayed by HPLC. The antibiotic L 17054 containing fractions (70 to 96) are pooled and the acetonitrile is removed. The residual aqueous solution is applied to a column of silanized silica gel (10 g; Merck 0.06–0.2 mm) in distilled water. After washing with water until the salts are completely eliminated, the product is eluted with a mixture acetonitrile/water, 1:1. The collected solution is concentrated to a small volume and a solid is precipitated by adding acetone. Upon drying at room temperature 2.4 g of essentially pure antibiotic L 17054 is obtained. By essentially following the above procedure but using a mixture of teicoplanin factor $A_2$ and $A_3$, teicoplanin factor $A_2$ component 1, teicoplanin factor $A_2$ component 2, teicoplanin factor $A_2$ component 3, teicoplanin factor $A_2$ component 4 and teicoplanin factor $A_2$ component 5 as the starting material, the same final product is obtained in essentially the same yields.

We claim:

1. A process for preparing an antibiotic substance selected from antibiotic L 17054 and its pharmaceutically acceptable addition salts which, in the non-salt form, is characterized by:
    (a) the specific rotation $[\alpha]_D^{20}$ is $-34°$ (c=1%, DMF)
    (b) it is freely soluble in water at pH>8.0, in dimethylformamide, dimethylsulfoxide, propyleneglycol and methylcellosolve; slightly soluble in methanol; almost insoluble in ethyl ether and acetone
    (c) an ultraviolet absorption spectrum which has the following absorption maxima:
    in 0.1N hydrochloric acid:
    $\lambda_{max}$ 278 nm ($E_1$ cm$^{1\%}$=60.6)
    in 0.1N sodium hydroxide:
    $\lambda_{max}$ 297 nm ($E_1$ $_{cm}$$^{1\%}$=118.8)
    in phosphate buffer pH 7.4:
    $\lambda_{max}$ 277 nm ($E_1$ $_{cm}$$^{1\%}$=70.3)
    (d) an infrared absorption spectrum in nujol with the following absorption maxima (cm$^{-1}$): 3700–2000, 29700–2850 (nujol), 1655, 1610, 1595, 1515, 1490, 1460 (nujol), 1375 (nujol), 1300, 1230, 1145, 1060, 1020, 970, 890, 850, 820, 720 (nujol)
    (e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67; ashes 0.2%
    (f) it has the following $R_f$ values in the TLC systems indicated below:

| Elution system (v/v) | $R_f$ value |
|---|---|
| (I) Acetonitrile/water 75:25 (silica gel Merck 60 $F_{254}$) | 0.32 |
| (II) Acetonitrile/5% aqueous sodium sulfate 30:70 (silica gel Merck silanized 60 $F_{254}$) Visualization: UV-light at 254 nm; 3% ethanolic ninhydrine 1% methanolic fluorescamine; | 0.61 |

(g) a retention time ($t_R$) of 8.3 minutes when analyzed by HPLC using a 150×4.0 mm Zorbax® ODS (5–6 μm) column (Zorbax is a trademark of the Dupont Co. for an octadecylsilane silica gel matrix), and eluting with a linear gradient from 0% to 50% solution B in solution A in 40 minutes (solution A: 25 mM $NaH_2P_4$/acetonitrile 9:1, buffered at pH 6.0 with 0.1N NaOH; solution B: 25 mM $NaH_2PO_4$/acetonitrile 3:7, buffered at pH 6.0 with 0.1N NaOH), with a flow rate of 2 ml/min.; (internal standard: 3,5-dihydroxytoluene $t_R$ 5.60 minutes)

(h) the $^1H$ NMR spectrum is registered at 270 MHz in DMSO-$d_6$ at 60° C. and with a sample concentration of 20 mg/ml (internal standard TMS, δ=0.00 ppm); some of the $^1H$ NMR data obtained after $D_2O$ exchange and selective decoupling experiments are as follows (δppm, multiplicity): 1.88, s; 2.85, d; ~3.5, dd; 3–4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.85, s; 8.42, d (i) a potentiometric titration profile which shows three titration slopes with pH½ values equal to 5.0 (one equivalent), 7.0 (one equivalent), and 11 (five equivalents) in methylcellosolve/water 4:1 upon titrating a solution of the test compound containing an excess of 0.01N HCl in methylcellosolve/water 4:1 with 0.01N NaOH in the same solvent mixture (l) an acidic function capable of forming salts (m) a basic function capable of forming salts (n) two sugar residues which are α-D-mannose and N-acetyl-β-D-glucosamine which comprises submitting a crude or essentially pure preparation of the antibiotic teicoplanin, a factor or component thereof or a mixture of said factors or components in any proportion to controlled acid hydrolysis in a strongf concentrated aqueous organic acid at about room temperature.

2. A process as in claim 1 wherein the strong concentrated aqueous organic acid is aqueous trifluoroacetic acid at a concentration between 75% and 95%.

3. A process as in claim 1 wherein the concentration of the aqueous trifluoroacetic acids is about 90%.

4. A process as in claim 1 wherein the reaction temperature is 10°–50° C.

5. A process as in claim 1 wherein the reaction temperature is 15°–35° C.

6. A process as in claim 1 wherein the reaction temperature is 20°–30° C.

7. A process as in claim 1 wherein the purification of the recovered antibiotic substance is made by using reverse-phase column chromatography.

8. A process as in claim 1 wherein the purification of the recovered antibiotic substance is made by reverse-phase column chromatography using a silanized silica gel having a distribution particle size of 0.06–0.2 mm as the stationary phase and eluting with binary mixtures of aqueous solutions of ammonium salts of organic acids and acetontrile or water soluble lower alkanols.

9. A process for preparing an antibiotic substance selected from antibiotic L 17054 and its pharmaceutically acceptable addition salts which, in the non-salt form, has the following formula:

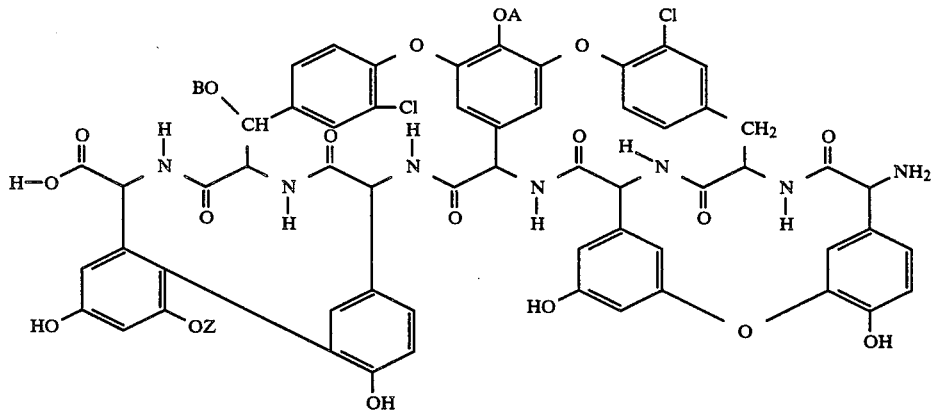

wherein A represents hydrogen, B is N-acetyl-β-D-glucosaminyl and Z is α-D-mannosyl, which comprises submitting a crude or essentially pure preparation of the antibiotic teicoplanin, a factor or component thereof or a mixture of said factors or components in any proportion to controlled acid hydrolysis in a strong concentrated aqueous organic acid at about room temperature.

* * * * *

UNITED STATES PATENT AND TRADEMARK OFFICE
CERTIFICATE OF CORRECTION

PATENT NO. : 4,594,187

DATED : June 10, 1986

INVENTOR(S) : P. Strazzolini et al.

It is certified that error appears in the above-identified patent and that said Letters Patent is hereby corrected as shown below:

At column 4, line 54, the patent reads "7.50, d; 7.64, d;" and should read --7.50, d; 7.56, d; 7.64, d;--

At column 8, line 8, the patent reads "stronqf" and should read --strong--

Signed and Sealed this

Eighth Day of January, 1991

*Attest:*

HARRY F. MANBECK, JR.

*Attesting Officer*      *Commissioner of Patents and Trademarks*